(12) United States Patent
Gawande et al.

(10) Patent No.: US 9,622,481 B2
(45) Date of Patent: *Apr. 18, 2017

(54) BIOFILM-REMOVING ANTIMICROBIAL COMPOSITIONS AND USES THEREOF

(71) Applicant: Kane Biotech Inc., Winnipeg (CA)

(72) Inventors: Purushottam Gawande, Winnipeg (CA); Srinivasa Madhyastha, Winnipeg (CA); Karen Lovetri, Winnipeg (CA); Nandadeva Yakandawala, Winnipeg (CA); Gord Froehlich, Selkirk (CA)

(73) Assignee: Kane Biotech Inc., Winnipeg (CA)

( * ) Notice: Subject to any disclaimer, the term of this patent is extended or adjusted under 35 U.S.C. 154(b) by 0 days.

This patent is subject to a terminal disclaimer.

(21) Appl. No.: 14/267,128

(22) Filed: May 1, 2014

(65) Prior Publication Data
US 2014/0322351 A1    Oct. 30, 2014

Related U.S. Application Data

(63) Continuation-in-part of application No. 13/145,991, filed as application No. PCT/CA2010/000067 on Jan. 22, 2010, now Pat. No. 8,753,692.

(60) Provisional application No. 61/146,852, filed on Jan. 23, 2009.

(51) Int. Cl.
| *A01N 59/12* | (2006.01) |
| *A01N 33/12* | (2006.01) |
| *A61K 33/18* | (2006.01) |
| *A01N 59/16* | (2006.01) |
| *A61K 31/513* | (2006.01) |
| *A01N 47/44* | (2006.01) |
| *A61K 31/155* | (2006.01) |
| *A01N 37/18* | (2006.01) |
| *A01N 43/54* | (2006.01) |
| *A61K 33/38* | (2006.01) |
| *A61K 38/17* | (2006.01) |
| *A61L 2/18* | (2006.01) |
| *A61L 2/22* | (2006.01) |
| *C02F 1/50* | (2006.01) |
| *C02F 5/10* | (2006.01) |

(52) U.S. Cl.
CPC .............. *A01N 59/12* (2013.01); *A01N 33/12* (2013.01); *A01N 37/18* (2013.01); *A01N 43/54* (2013.01); *A01N 47/44* (2013.01); *A01N 59/16* (2013.01); *A61K 31/155* (2013.01); *A61K 31/513* (2013.01); *A61K 33/18* (2013.01); *A61K 33/38* (2013.01); *A61K 38/17* (2013.01); *A61L 2/186* (2013.01); *A61L 2/22* (2013.01); *A61L 2202/24* (2013.01); *C02F 1/50* (2013.01); *C02F 1/505* (2013.01); *C02F 5/105* (2013.01); *C02F 2303/20* (2013.01)

(58) Field of Classification Search
None
See application file for complete search history.

(56) References Cited

U.S. PATENT DOCUMENTS

| 3,170,840 A | 2/1965 | Timm |
| 4,554,154 A | 11/1985 | White |
| 4,961,417 A | 10/1990 | Young et al. |
| 5,019,096 A | 5/1991 | Fox, Jr. et al. |
| 5,089,205 A | 2/1992 | Huang et al. |
| 5,165,952 A | 11/1992 | Solomon et al. |
| 5,362,754 A | 11/1994 | Raad et al. |
| 5,451,424 A | 9/1995 | Solomon et al. |
| 5,549,919 A | 8/1996 | Ueno et al. |
| 5,616,338 A | 4/1997 | Fox, Jr. et al. |
| 5,688,516 A | 11/1997 | Raad et al. |
| 5,779,960 A | 7/1998 | Berlowitz-Tarrant et al. |
| 6,187,768 B1 | 2/2001 | Welle et al. |
| 6,261,271 B1 | 7/2001 | Solomon et al. |
| 6,475,434 B1* | 11/2002 | Darouiche ............ A61L 2/0082 422/28 |
| 6,589,591 B1 | 7/2003 | Mansouri et al. |
| 6,706,024 B2 | 3/2004 | Modak et al. |
| 6,843,784 B2 | 1/2005 | Modak et al. |
| 7,282,214 B2 | 10/2007 | Willcox et al. |
| 7,329,412 B2 | 2/2008 | Modak et al. |
| 2005/0191333 A1 | 9/2005 | Hsu |
| 2007/0003538 A1 | 1/2007 | Madhyastha |
| 2008/0139450 A1 | 6/2008 | Madhyastha et al. |

FOREIGN PATENT DOCUMENTS

| CA | 2612729 A1 | 1/2007 |
| CN | 1418617 A | 5/2003 |
| EP | 2098942 A1 | 9/2009 |
| JP | 2004-315472 A | 11/2004 |
| WO | 02/45575 A2 | 6/2002 |
| WO | 2005/018701 A1 | 3/2005 |

OTHER PUBLICATIONS

Gawande, P. V.; et al. "Antibiofilm activity of sodium bicarbonate, sodium metaperiodate and SDS combination against . . . " Journal of Applied Microbiology, 2008, 105, 986-992.*

(Continued)

*Primary Examiner* — Mina Haghighatian
*Assistant Examiner* — Erin Hirt
(74) *Attorney, Agent, or Firm* — Ridout & Maybee LLP

(57) ABSTRACT

The present invention provides novel compositions comprising: (a) a metaperiodate and (b) chlorhexidine or a chlorohexidine salt and uses thereof for the preparation of devices, and in particular medical devices, susceptible to colonization by biofilm forming bacteria.

11 Claims, 9 Drawing Sheets

(56) References Cited

OTHER PUBLICATIONS

Wirthlin, MR; et al. "A laboratory model biofilm fermenter: design and initial trial on a single species biofilm." J. Periodontol., 2005, 76, Abstract only.*
Parkar, S. G.; et al. "Physiology of biofilms of thermophilic bacilli . . . " J. Ind. Microbiol. Biotechnol., 2003, pp. 553-560.*
Burton et al., "Antibiofilm activity of GlmU enzyme inhibitors against catheter-associate uropathogens", Antimocrob. Agents Chemother., 50: 1835-1840, 2006.
Darouiche R. et al., "A comparison of two antimicrobial-impregnated central venous catheters. Catheter study group", New England Journal of Medicine, 340(1):1-8, Jan. 7, 1999.
Darouiche R. et al., "Antimicrobial activity and durability of a novel antimicrobial-impregnated bladder catheter", International Journal of Antimicrobial Agents, 8:243-247, 1997.
Darouiche R. et al., "Efficacy of antimicrobial-impregnated bladder catheters in reducing catheter-associated bacteriuria: a prospective, randomized, multicenter clinical trial", Urology, 54(6):976-981, 1999.
Davies, D., "Understanding biofilm resistance to antibacterial agents", Nature Reviews Drug Discovery, V.2, 114-122, 2003.
Fallgren C. et al., "In vitro Anti-Staphylococcal Activity of Heparinized Biomaterials bonded with Combinations of Rifampicin", Zent. BL. Bakteriol, 287:19-31, 1998.
Gilbert P. & Allison D.G., "Preservation of Pharmaceutical Products", Encyclopedia of Pharmaceutical Technology (3rd Edition), p. 2983-2992, Oct. 2, 2006. DOI: 10.1081/E-EPT-100200009.
Johnson J. et al., "Activities of a Nitrofurazone-Containing Urinary Catheter and a Silver Hydrogel Catheter against Multidrug-Resistant Bacteria Characteristic of Catheter-Associated Urinary Tract Infection", Antimicrobial Agents and Chemotherapy, 43(12):2990-2995, Dec. 1999.
Karpanen et al. "Antimicrobial efficacy of chlorhexidine digluconate alone and in combination with eucalyptus oil, tea tree oil, and thymol against planktonic and biofilm cultures of *Streptococcus epidermis*", J. Antimicrob. Chemother., 62: 1031-1036, 2008.
Kim et al., "Synergistic Inhibitory Effect of Cationic Peptides and Antimicrobial Agents on the Growth of Oral Streptococci", Caries Res., 37:425-430, 2003.
Kim, C. et al., "Evaluation of an antimicrobial-impregnated continuous ambulatory peritoneal dialysis catheter for infection in control in rats", American Journal of Kidney Disease, 39(1):165-173, Jan. 2002.
Kuyyakanond T. and Quesnel K.B., "The mechanism of action of chlorhexidine", FEMS Microbiol. Lett., 100: 211-216, 1992.
Logghe C. et al., "Evaluation of chlorhexidine and silver-sulfadiazine impregnated central venous catheters for the prevention of bloodstream infection in leukaemic patients: a randomized controlled trial", J Hosp. Infect., 37: 145-156, 1997.
McDonnell, G. et al., "Antiseptics and Disinfectants: Activity, Action and Resistance", Clinical Microbiology Reviews, 147-179, 1999.
Pons et al., "Evaluation of antimicrobial interactions between chlorhexidine quarternary ammonium compounds, preservatives and excipients", J. Appl. Bacteriol, 73: 395-400, 1992.
Raad I. et al., "Antimicrobial durability and rare ultrastructural colonization of indwelling central catheters coated with minocycline and rifampin", Critical Care Medicine, 26(2):219-224, Feb. 1998.
Raad I. et al. "Minocycline and Ethylenediaminetetraacetate for the Prevention of Recurrent Vascular Catheter Infections", Clinical Infectious Diseases, 25:149-151, 1997.
Richards G. et al., "The Effect of Protamine on Antibiotic Action Against *Staphylococus* Epidermidis Biofilms" ASAIO Transactions, 36:296-299, 1990.
Schierholz J. et al., "Controlled release of antibiotics from biomedical polyurethanes: morphological and structural features", Biomaterials, 18(12):839-844, 1997.
Sherertz R. et al., "Efficacy of Dicloxacillin-Coated Polyurethane Catheters in Preventing Subcutaneous *Staphylococcus aureus* Infection in Mice", Antimicrobial Agents and Chemotherapy, 33(8):1174-1178, Aug. 1989.
Soboh F. et al. "Effects of Ciprofloxacin and Protamine Sulfate Combinations against Catheter-Associated *Pseudomonas aeruginosa* Biofilms", Antimicrobial Agents and Chemotherapy, 39(6):1281-1286, Jun. 1995.
Stickler D., "Biomaterials to prevent nosocomial infections: is silver the gold standard?", Current Opinion in Infectious Disease, 13:389-393, 2000.
Tunney M. et al., "Infection associated with medical devices", Reviews in Medical Microbiology, 7(4):195-205, 1996.
Wang, X et al., "The pgaABCD Locus of *Escherichia coli* Promotes the synthesis of a polysaccharide adhesion required for biofilm formation", Journal of Bacteriology, v. 186, issue 9, 2724-2734, 2004.
Yakandawala et al., "Effect of ovotransferrin, protamine sulfate, and EDTA combination on biofilm formation by catheter associated bacteria", J. Appl. Microbiol., 102: 722-727, 2007.
International Search Report (Form PCT/ISA/210) for corresponding International App. No. PCT/CA2010/000067.
Written Opinion (Form PCT/ISA/237) for corresponding International App. No. PCT/CA2010/000067.

* cited by examiner

BIOFILM-REMOVING ANTIMICROBIAL COMPOSITIONS AND USES THEREOF

CROSS REFERENCE TO RELATED APPLICATION

This application is a continuation-in-part of U.S. application Ser. No. 13/145,991 filed Sep. 8, 2011, which is a national phase of International Patent Application No. PCT/CA2010/000067 filed Jan. 22, 2010, which claims priority from U.S. Application No. 61/146,852 filed Jan. 23, 2009, all of which are incorporated by reference herein in their entirety.

FIELD OF THE INVENTION

The present invention relates to novel antimicrobial compositions that inhibit growth and proliferation of biofilm embedded microorganisms, and methods/uses thereof.

BACKGROUND

Biofilms are medically and industrially important because they can accumulate on a wide variety of substrates and are resistant to antimicrobial agents and detergents. Microbial biofilms develop when microorganisms adhere to a surface and produce extracellular polymers that facilitate adhesion and provide a structural matrix. Therefore inhibiting adhesion to surfaces is important. This surface may be inert, non-living material or living tissue.

A method of long-term prevention from biofilm formation is needed. Also needed is a composition that allows for low quantities of a composition to be used effectively to reduce toxicity or other side effects to a user or patient. There is also a need for compositions that are medically acceptable, effective at lower concentrations, free of resistance and relatively economical to manufacture on a commercial scale for reducing biofilm formation in biomedical devices.

SUMMARY OF THE INVENTION

An embodiment of the invention includes a composition for inhibiting microbial biofilms comprising: (a) a cationic peptide and (b) a quaternary ammonium compound, a silver containing particle, or 5-fluorouracil.

A cationic peptide includes omiganan, protamine, Cecropin A, or a combination thereof. A cationic peptide can be low molecular weight derivatives or salts of protamine such as protamine sulfate. A composition comprising protamine sulfate can include comprise about 100 µg/ml to about 1000 µg/ml of protamine sulfate. In an embodiment, the composition can be concentrated and then diluted prior to use.

Quaternary ammonium compounds can be derivatives or salts of benzalkonium such as benzalkonium chloride. The amount of benzalkonium chloride included in the composition can be about 20 µg/ml to about 200 µg/ml. In an embodiment, the composition can be concentrated and then diluted prior to use.

The amount of 5-fluoruracil included in the composition can comprise about 50 µg/ml to about 5000 µg/ml of 5-fluoruracil. In an embodiment, the composition can be concentrated and then diluted prior to use.

Silver containing particles includes a silver nanoparticle or silver sulfadiazine. The amount of silver included in the composition can comprise about 1 µg/ml to about 1000 µg/ml of silver. In an embodiment, the composition can be concentrated and then diluted prior to use.

An embodiment of the invention includes a composition for inhibiting microbial biofilms comprising: (a) a metaperiodate and (b) 5-fluorouracil, silver containing particle, chlorhexidine, or triclosan.

The amount of chlorhexidine included in the composition can comprise about 1 µg/ml to about 100 µg/ml of chlorhexidine. In an embodiment, the composition can be concentrated and then diluted prior to use.

Metaperiodate can be sodium or potassium meta-periodate. The amount of sodium metaperiodate included in the composition can comprise about 20 µg/ml to about 2000 µg/ml of meta-periodate. In an embodiment, the composition can be concentrated and then diluted prior to use.

The concentration of chlorhexidine or chlorhexidine salt may be about 10 µg/ml to about 10000 µg/ml chlorhexidine or chorhexidine salt, about 100 µg/ml to about 5000 µg/ml chlorhexidine or chorhexidine salt, or about 1000 µg/ml to about 5000 µg/ml chlorhexidine or chorhexidine salt, about 100 µg/ml to about 1000 µg/ml chlorhexidine or chorhexidine salt, or about 500 µg/ml chlorhexidine or chorhexidine salt.

A composition according to the invention can be effective against biofilms produced by microbial species including *S. epidermidis, E. faecalis, E. coli, P. mirabilis, P. aeruginosa, K. pneumoniae, S. aureus, S. viridans, K. oxytoca, S. saprophyticus, Legionella pneumophila, Mycobacterium* spp., *Citrobacter freundii, Aeromonas hydrophile, Fusobacterium nucleatum,* Vancomycin resistant *Enterococcus faecalis* (VRE), *Enterococcus faecium, Actinomyces naeslundii, Enterobacter cloacae, Providencia stuartii, Serratia marcescens,* or combinations thereof. In a further embodiment of the invention, the composition is effective against biofilms produced by gram-negative bacterial species.

In another embodiment of the invention, a composition can be effective against biofilms produced by gram-positive bacterial species.

In yet another embodiment of the invention, a composition can be effective against biofilms produced by fungal species, including *C. albicans*.

In another embodiment, a method comprises administering a composition of the invention to disinfect an article of matter, such as dental instruments, medical instruments, medical devices, surfaces (e.g., tabletop, countertop, bathtub, tile, etc.), tubing, and the like. A composition of the invention can comprise a compound of the invention and common household disinfectants.

A method of the invention includes rinsing, coating a surface, or impregnating a surface of an object with at least one surface. An object can include a medical device including disposable or permanent or indwelling catheters, long term urinary devices, tissue bonding urinary devices, wound drain tubes, ventricular catheters, endotracheal tubes, breathing tubes, feeding tubes, dairy lines, and drinking water lines. Furthermore, a method of the invention includes cleaning pipelines in industries such as food and beverage industries, paper mills, cooling towers, and gas and oil industries.

In yet another embodiment, a method comprises treating wounds by administering a composition of the invention, wherein the wounds include, but are not limited to, cutaneous abscess, surgical wounds, sutured lacerations, contaminated lacerations, burn wounds such as partial and full thickness burns, decubitus ulcers, stasis ulcers, leg ulcers, foot ulcers, venous ulcers, diabetic ulcers, ischemic ulcers, and pressure ulcers.

One embodiment of the present invention includes a method comprising coating treating, or impregnating composition in wound care devices such as non-resorbable gauze/sponge dressing, hydrophilic wound dressing, occlusive wound dressing, hydrogel wound, and burn dressing. The present invention also includes use of a spray-applicator containing a composition of the invention as a wound care device.

A method of the invention also includes treating a patient with a microbial infection by administering a composition of the invention, wherein the composition is coated or impregnating on the surface of an object. An object can be a wound care device such as non-resorbable gauze/sponge dressing, hydrophilic wound dressing, occlusive wound dressing, hydrogel wound, and burn dressing. The present invention also includes use of a spray-applicator containing a composition of the invention as a wound care device.

DETAILED DESCRIPTION OF THE INVENTION

Figure 1:
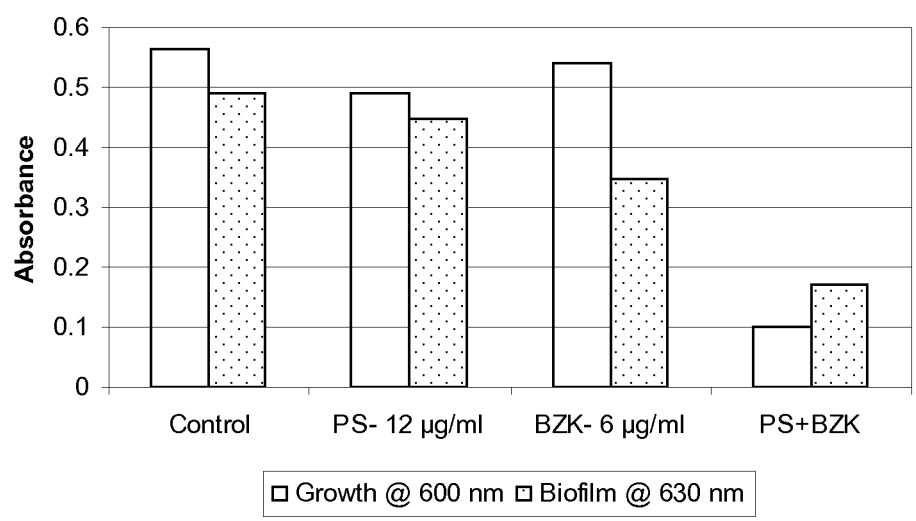
FIG. 1 is a bar graph illustrating the effect of control (solution without an active ingredient), 12 µg/ml of protamine sulfate (PS), 6 µg/ml of benzalkonium chloride (BZK) and a combination of 12 µg/ml protamine sulfate and 6 µg/ml benzalkonium chloride (PS+BZK) on growth and biofilm formation of Escherichia coli.

Antimicrobial compositions have found an increasing number of commercial and consumer uses. An effective antimicrobial composition, such as a composition that inhibits growth and proliferation of biofilm embedded microorganisms, is useful in a plethora of applications. Such an antimicrobial composition can either be used on its own, incorporated into a consumable, or incorporated into a surface desirable to be free of bacteria.

Definitions

The term "antimicrobial" refers to a compound or a composition that kills or slows/stops the growth of microorganisms, including, but not limited to bacteria and yeasts.

The term "biofilm embedded microorganisms" refers to any microorganism that forms a biofilm during colonization and proliferation on a surface, including, but not limited to, gram-positive bacteria (e.g., S. epidermidis), gram-negative bacteria (e.g., P. aeruginosa), and/or fungi (e.g., C. albicans).

The term "biofilm formation" refers to the attachment of microorganisms to surfaces and the subsequent development of multiple layers of cells.

The term "inhibition" or "inhibiting" refers to a decrease of biofilm associated microorganism formation and/or growth. The microorganisms can include bacteria (e.g., streptococci) or fungi (e.g., Candida spp.)

"Modulating detachment" refers to increasing or decreasing bacterial or fungal biofilm detachment or release of bacterial or fungal cells from a biofilm. Further, "modulating detachment", is also inclusive of changes in the ability of the bacteria or fungal to attach as a biofilm.

The term "mammal" for purposes of treatment refers to any animal classified as a mammal, including humans, domestic, farm, sport and zoo animals, or pet animals, such as dogs, horses, cats, cattle, pigs, sheep, etc.

The term "therapeutically effective amount" refers to an amount of a composition of the invention effective to "alleviate" or "treat" a disease or disorder in a subject or mammal. A "therapeutically effective amount" as used herein also includes an amount that is bacteriostatic or bacteriocidal, for example, an amount effective for inhibiting growth of biofilm associated bacteria or killing biofilm associated bacteria, respectively.

A "therapeutically effective amount" as used herein also includes an amount that is fungistatic or fungicidal, for example, an amount effective for inhibiting further growth of biofilm associated fungi or killing biofilm associated fungi, respectively. By administering the composition suitable for use in methods of the invention concurrently with an antimicrobial compound, the therapeutic antimicrobial compound may be administered in a dosage amount that is less than the dosage amount required when the therapeutic antimicrobial compound is administered as a sole active ingredient. By administering lower dosage amounts of the active ingredient, the side effects associated therewith should accordingly be reduced.

A "prophylactically effective amount" as used herein includes an amount effective for preventing or protecting against infectious diseases, and symptoms thereof, and amounts effective for alleviating or treating infectious diseases, related diseases, and symptoms thereof.

The term "treatment", "treating", or "alleviating" refers to an intervention performed with the intention of altering or inhibiting the pathology of a disorder.

The term "preventing" or "prophylaxis" refers to preventing disease, pathology, and/or symptoms.

The term "dental caries" refers to a localized destruction of tissues of a tooth by acid produced from bacterial degradation of fermentable sugars. The chief etiological agent of dental caries is *S. mutans*. Degradation of fermentable sugars by *S. mutans* on the tooth surface produces an acid that destroys oral tissues, and more particularly, enamel and dentin.

The term "dental plaque" is a general term for the diverse microbial community (predominantly bacteria) found on the tooth surface, embedded in a matrix of polymers of bacterial and salivary origin. Further, "dental plaque-associated *S. mutans*" refers to *S. mutans* that is a component of the dental plaque.

The term "endocarditis" refers to an infection of the endocardial surface of the heart, which may include one or more heart valves, the mural endocardium, or a septal defect.

The term "gingivitis" refers to inflammation of gingival tissue without loss of connective tissue.

The term "oral diseases" refers to diseases and disorders affecting the oral cavity or associated medical conditions. Oral diseases include, but are not limited to, dental caries; periodontal diseases (e.g., gingivitis, adult periodontitis, early-onset periodontitis, etc.); mucosal infections (e.g., oral candidiasis, herpes simplex virus infections, recurrent aphthous ulcers, etc.); oral and pharyngeal cancers; and precancerous lesions.

The term "periodontal disease" refers to an inflammatory process of the gingival tissues and/or periodontal membrane of the teeth, resulting in a deep gingival sulcus, possibly producing periodontal pockets and loss of alveolar bone.

The term "periodontitis" refers to inflammation and loss of connective tissue of the supporting or surrounding structure of teeth with loss of attachment.

The term "chronic wound" refers to a wound that fails to progress through an orderly and timely sequence of repair or a wound that does not respond to treatment and/or the demands of treatment are beyond the patient's physical health, tolerance or stamina. Many wounds that are first considered to be acute wounds ultimately become chronic wounds due to factors still not well understood. One significant factor is the transition of planktonic bacteria within the wound to form a biofilm.

In the context of wound treatment, "biofilm disruption" or "inhibition of biofilm reconstitution" refers to biofilm clearance from a chronic or acute wound, or to inhibit reconstitution of a biofilm mass from remnants remaining after debridement and thereby promote healing of a wound.

Compositions

An embodiment of the invention includes a composition for inhibiting or disrupting microbial biofilms comprising: (a) a cationic peptide and (b) a quaternary ammonium compound, a silver containing particle or antineoplastic agents. A cationic peptide includes omiganan, protamine, Cecropin A, or a combination thereof. A cationic peptide can also be a low molecular weight derivative or salt of protamine such as protamine sulfate.

A quaternary ammonium compound includes, but is not limited to, benzalkonium chloride, benzalkonium bromide, benzalkonium saccharinate, cetalkonium chloride, cetealkonium bromide, hydrogenated tallowalkonium chloride, tallowalkonium chloride, didecyldimethylammonium saccharinate, hex adecylpyridinium saccharinate, benzalkonium acesulfamate, didecyldimethylammonium acesulfamate, hexadecylpyridinium acesulfamate, 3-hydroxy-1-octyloxymethylpyridinium acesulfamate, 3-hydroxy-1-octyloxymethylpyridinium saccharinate, cetylpyridinium chloride, or a combination thereof. In an embodiment of the invention, a quaternary ammonium compound comprises benzalkonium chloride.

A silver containing particle can be silver nanoparticles or silver sulfadiazine.

An embodiment of the invention also includes a composition for inhibiting or dispersing microbial biofilms comprising: (a) an antibiofilm compound and (b) antineoplastic agent, silver containing particle, bis-guanide, or triclosan. An antibiofilm compound includes protamine sulfate, metaperiodate, N-acetylecysteine, ethylenediaminetetraacetic acid (EDTA), ovotransferrin, lactoferrin, proteolytic and polysaccharide degrading enzymes, RNAIII inhibitory peptide (RIP), or gallium. In an embodiment of the invention, an antibiofilm compound comprises sodium or potassium metaperiodate.

An antineoplastic agent can be mitomycin c, 5-fluorouracil, bleomycin, doxorubicin, or a combination thereof. In a preferred embodiment, the antineoplastic agent is comprises 5-fluorouracil.

A bis-guanide compound can be chlorhexidine (its base or salts), alexidine, or polyhexamethylene biguanides.

A composition comprising benzalkonium chloride includes, for example, between 20 µg/ml to 200 µg/ml of benzalkonium chloride. The higher end of this stated range can be used to prepare a concentrated product that would be diluted prior to use.

The amount of 5-fluoruracil included in the composition can comprise about 50 µg/ml to about 5000 µg/ml of 5-fluoruracil. In an embodiment, the composition can be concentrated and then diluted prior to use.

The amount of chlorhexidine included in the composition can comprise about 1 µg/ml to about 100 µg/ml of chlorhexidine. In an embodiment, the composition can be concentrated and then diluted prior to use.

Silver containing particles can include a silver nanoparticle or silver sulfadiazine. The amount of silver included in the composition can comprise about 1 µg/ml to about 1000 µg/ml of silver. In an embodiment, the composition can be concentrated and then diluted prior to use.

Metaperiodate can be sodium or potassium meta-periodate. The amount of sodium metaperiodate included in the composition can comprise about 20 µg/ml to about 2000 µg/ml of meta-periodate. The higher end of this stated range can be used to prepare a concentrated product that would be diluted prior to use.

In an embodiment of the invention, a composition according to the invention is effective against biofilms produced by microbial species such as *S. epidermidis, E. faecalis, E. coli, P. mirabilis, P. aeruginosa, K. pneumoniae, S. aureus, S. viridans, K. oxytoca, S. saprophyticus, L. pneumophila, Mycobacterium* spp., *C. freundii, A. hydrophile, F. nucleatum, A. naeslundii, P. stuartii, S. marcescens*, or combinations thereof. In a further embodiment of the invention, a composition is effective against biofilms produced by gram-negative bacterial species.

In another embodiment of the invention, a composition is effective against biofilms produced by gram-positive bacterial species.

In yet another embodiment of the invention, a composition is effective against biofilms produced by fungal species, including *C. albicans*.

Compositions described herein have enhanced antibiofilm activity when combined. Enhanced antibiofilm activity is evidenced by the small quantities of each of these compounds that can be used to produce an effective antimicrobial composition, less than would be required if any of the compounds were to be used on their own. Low levels and increased efficacy of the active compounds or ingredients make this invention very desirable and relatively economical to manufacture. Thus, typical bacterial resistances for antibiotics may not develop.

Higher concentrations of these compounds can be used if it is desired for certain applications and will depend on the bacteria targeted and the device to be treated. Lower concentrations of compounds may also be used in certain situations.

While the active components discussed herein may be 100% of the composition of the invention, a composition can contain from at least about 1% to about 50% of active components by weight based upon total weight of the composition of the invention being employed. In one embodiment, a composition comprises from at least about 0.5% to about 25% (by weight) active components.

Compositions of the invention may include any number of well known active components and base materials. Compositions may further comprise ingredients such as, but not limited to: suitable solvents such as water, and ethanol; antimicrobials such antibacterials and antifungals; binding, bonding, coupling agent, or cross-linking agent; or a pH adjuster.

Other possible components of the composition include, but are not limited to buffer solutions, phosphate buffered saline, saline, water, polyvinyl chloride, polyethylene, polyurethane, polypropylene, silicone (e.g., silicone elastomers and silicone adhesives), polycarboxylic adds, (e.g., polyacrylic add, polymethacrylic add, polymaleic add, poly-(maleic acid monoester), polyaspartic acid, polyglutamic acid, aginic acid or pectimic acid), polycarboxylic acid anhydrides (e.g., polymaleic anhydride, polymethacrylic anhydride or polyacrylic acid anhydride), polyamines, polyamine ions (e.g., polyethylene imine, polyvinylamine, polylysine, poly-(dialkylamineoethyl methacrylate), poly-(dialkylaminomethyl styrene) or poly-(vinylpyridine)), polyammonium ions (e.g., poly-(2 methacryloxyethyl trialkyl ammonium ion), poly-(vinylbenzyl trialkyl ammonium ions), poly-(N.N.-alkylypyridinium ion) or poly-(dialkyloctamethylene ammonium ion) and polysulfonates (e.g. poly-(vinyl sulfonate) or poly-(styrene sulfonate)), collodion, nylon, rubber, plastic, polyesters, polyethylene terephthalate optionally sealed with gelatin, collagen, or albumin, polytetrafluoroethylene, latex, and derivatives thereof, elastomers, cyanoacrylates, methacrylates, papers with porous barrier films, adhesives, e.g., hot melt adhesives, solvent based adhesives, and adhesive hydrogels, fabrics, and crosslinked and non-crosslinked hydrogels, and any other polymeric materials which facilitate dispersion of the active components and adhesion of the biofilm penetrating coating to at least one surface of the medical device. Linear copolymers, cross-linked copolymers, graft polymers, and block polymers, containing monomers as constituents of the above-exemplified polymers may also be used.

In another embodiment, the composition can further comprise one or more disinfecting agents. Disinfects can comprise alcohols (such as ethanol or isopropanol), aldehydes (such as glutaraldehyde), oxidizing agents (such as sodium hypochlorite, calcium hypochlorite, chloramine, hydrogen peroxide, iodine, peracetic acid, performic acid, potassium permanganate, and potassium peroxymonosulfate), phenolics (such as phenol, o-phenylphenol, chloroxylenol, hexachlorophene, and thymol). A disinfectant can be a spray or a liquid. A disinfectant can be concentrated or ready-to-use. A disinfectant can be for commercial or household use. A composition of the invention can also be incorporated into household disinfectants, laundry detergent, and household cleaning solutions.

Biofilm on Surfaces

Biofilms accumulate on the surface of various objects such as medical devices, tubing, pipelines, counter/tabletops, filters, water lines, and tiles of various kinds.

Biofilms on indwelling medical devices may be composed of gram-positive or gram-negative bacteria or yeasts. Bacteria commonly isolated from these devices include (a) gram-positive *Enterococcus faecalis*, Vancomycin resistant *Enterococcus faecalis, Staphylococcus epidermidis, Staphylococcus aureus*, and *Enterococcus faecium*; (b) gram-negative *Escherichia coli, Klebsiella pneumoniae, Proteus mirabilis, Enterobacter cloacae*, and *Pseudomonas aeruginosa*; and (c) fungal species, such as *Candida albicans*. The organisms most commonly isolated from urinary catheter biofilms are *S. epidermidis, E. faecalis, E. coli, mirabilis, P. aeruginosa* and *K. pneumoniae*. In the case of vascular catheters, *S. aureus* and *S. epidermidis* account for almost 70-80% of all infectious organisms, with *S. epidermidis* being the most common organism. *C. albicans* accounts for about 10-15% of catheter infections. Gram-negative bacilli account for almost 60-70%, Enterococci for about 25%, and *C. albicans* for about 10% of cases of urinary tract infections. Catheter-associated urinary tract infection is a very common nosocomial infection (about 1 million patients in US hospitals each year). It is the second most common cause of nosocomial infections (Maki and Tambyah, *Emerg. Infect. Dis.*, 7:1-6, 2001).

A composition of present invention can be useful for decontaminating, inhibiting growth, or preventing growth on surfaces where microorganisms form a biofilm, such as tubing. A method of the invention includes rinsing or decontaminating a surface by contacting the surface with a composition of the invention. Further, a method of the invention includes inhibiting biofilm growth or preventing biofilm growth by incorporating a composition of the invention into a surface. A composition of the invention can be incorporated into a surface by coating or impregnating the surface of the object.

A composition of the invention can coat, impregnate, flush, or rinse a surface of tubing or a medical device, especially an insertable medical device, Tubing includes, but is not limited to, disposable, permanent, and indwelling catheters, long term urinary devices, tissue bonding urinary devices, wound drain tubes, ventricular catheters, endotracheal tubes, breathing tubes, feeding tubes, dairy lines, oil and gas pipeline and drinking water lines. Some tubing can also be considered a medical device. Insertable medical devices include catheters, which can be inspected without invasive techniques such as endoscopy. Medical devices may be formed of any suitable metallic materials or non-metallic materials known to persons skilled in the art. Examples of metallic materials include, but are not limited to, tivanium, titanium, and stainless steel, and derivatives or combinations thereof, Examples of non-metallic materials include, but are not limited to, thermoplastic or polymeric materials such as rubber, plastic, polyesters, polypropylene, polycarbonate, polyvinyl chloride, nylon, polyethylene, polyurethane, silicone, polyethylene terephthalate, polytetrafluoroethylene, latex, elastomers and polyethylene terephthalate sealed with gelatin, collagen or albumin, and derivatives or combinations thereof. Medical devices include at least one surface for applying a composition of the invention. Preferably, a composition of the invention is applied to an entire medical device. Compositions can also be incorporated into polymers, which are used to form devices such as catheters by impregnating or by drug polymer conjugation.

Furthermore, a composition of the invention can also be used to clean pipelines in industries such as food and beverage industries, paper mills, cooling towers and gas and oil industries by contacting a surface with biofilm growth.

A composition of the invention can also be incorporated into vacuum systems and vacuum filters, paint and wall coverings, humidifiers and humidifier filters, and vacuum cleaners, toys incorporation into plastics for a variety of household items, including the inside and outside of washing machines, dishwashers, animal water dishes, bathroom tiles and fixtures, sealants and grout, towels, home and kitchen containers, dishes, cutting boards, dish drying trays, bathtubs including aerated bathtubs and hot tub spas, fish ponds, swimming pools, bird baths, garden hose, planters and hot tubs.

Industrial applications to antimicrobial compounds include their use in dairy lines, either as a flush or wash for such lines, or incorporated within the lines, for example as a coating; liquid distribution lines in the food and beverage manufacturing or dispensing, for example, use as a coating in feeder lines for high sugar or syrup distribution in the manufacturing of soft drinks; pulp and paper mills (for biofouling); in the manufacturing and containment of cosmetics from production line equipment down to the end consumable, either incorporated within the cosmetic or coated on the jar containing the cosmetic; in water treatment facilities; in the leaching process used in mining; to prevent corrosion caused or accelerated by organisms, in oil and gas pipelines, in the souring of oil fields, and in cooling towers.

Consumer and light commercial uses of antimicrobial agents include their incorporation in general household disinfectants; laundry detergent; cleaning supplies; equipment involved in the leeching process or mining; wound care; a vacuum system; HVAC systems; vacuum cleaner bags; paint covering; wall coverings; window frames; doors; door frames; cooling towers; humidifiers; vacuum cleaners; filters such as a vacuum filter, a humidifier filter, hot tub filter, or a swimming pool filter; toys; cosmetic containers; plastic bottles; water jugs; a tap and water spout; incorporation into plastics for a variety of household items including the inside and outside of washing machines and dishwashers; animal water dishes; bathroom tiles and fixtures; sinks; showers; shower heads; toilets; toilets lids; toilet seats; sealants and grout; towels; home and kitchen containers; dishes; cups; utensils such as forks, spoons, knives, and spatulas; bowls; food storage containers; beverage storage containers; cutting boards; dish drying trays; garbage bags; bathtubs including whirlpool bathtubs and hot tub spas; sinks; showers; fish ponds; swimming pools; swimming pool liners; swimming pool skimmer; pond liners; bird baths; garden hose; water sprinkling lines; planters; and hot tubs. In another aspect, the present invention provides a composition suitable for coating an object which is desirable to be microorganism resistant, for example paint, wall covering, or protective plastic coating. The object may be any object which is desirable to be microorganism resistant, such as a home product, an industrial product, a medical product or medical device, a piece of apparel or a textile, a building product, etc.

An embodiment includes, a method to reduce, inhibit, or prevent a microbial biofilm comprising disinfecting, cleaning, or rinsing a surface by contacting said surface with a combination of a composition of the invention and a disinfectant. A combination of a composition of the invention and a disinfectant can also include a hydrophilic polymer. Preferably, the hydrophilic polymer is a nitrogen-containing polymer having surface-modifying properties. The method can also reduce, inhibit, or prevent deposits on a surface. Deposits can be lime scale, soap scum and other organically encrusted or flocculated deposits. A surface can be a hard surface, preferably silicone surface, more preferably a glass or ceramic surface, or metal surface.

A method of incorporating a composition of the invention into a surface of an object includes immersing or flushing, coating, drug-polymer conjugate and impregnating (Tunny et al., *Rev. Med. Microbiol.,* 74:195-205, 1996). In a clinical setting, suitable catheters can be treated by immersion immediately prior to placement, which offers flexibility and control to clinicians in certain situations.

Direct incorporation of a composition of the invention into a polymeric matrix of a medical device at the polymer synthesis stage or at the device manufacture stage is also possible (Schierholz et al., *Biomaterials,* 18:839-844, 1997).

In a preferred embodiment, an object, such as a medical device, is submerged in a composition for at least 5 minutes. Alternatively, an object may be flushed with a composition. When an object is tubing (e.g., dental unit waterline, a dairy line, a food and beverage processing line, etc.), a composition of the invention may be poured into the tubing and both ends of the tubing clamped such that the composition is retained within the lumen of the tubing. The tubing is then allowed to remain filled with the composition for a period of time sufficient to remove substantially all of the microorganisms from at least one surface of the object, generally, for at least about 1 minute to about 48 hours. Alternatively, tubing may be flushed by pouring a composition of the invention into the lumen of the tubing for an amount of time sufficient to prevent substantial growth of all biofilm embedded microorganisms. Such flushing may be required only once, or may be required at regular intervals over the lifetime of use of the tubing. Concentrations of active components in a composition may vary as desired or necessary to decrease the amount of time the composition is in contact with a medical device.

In another aspect, a method of the invention includes coating a medical device. Broadly, coating a medical device includes applying a composition coating to at least one surface of the medical device in an amount sufficient to substantially reduce growth, proliferation, or colonization of biofilm microorganisms on at least one surface of the medical device.

In one specific embodiment, at least one surface of a medical device is contacted with a composition of the invention under conditions wherein the composition of the invention covers at least one surface of the medical device. "Contacting" includes, but is not limited to, impregnating, compounding, mixing, integrating, coating, spraying and dipping.

In another embodiment of coating a medical device, combining active ingredients and a base material at room temperature and mixing a composition of the invention for a time sufficient to evenly disperse active agents in the composition prior to applying the composition to a surface of the device form the composition coating. A medical device may be contacted with a composition of the invention for a period of time sufficient for the composition to adhere to at least one surface of the device. After a composition of the invention is applied to a surface of the device, it is allowed to dry.

Although one layer or coating of the composition is believed to provide the desired composition coating, multiple layers or coatings can be applied. Multiple layers of a composition of the invention can be applied to the at least one surface of a medical device by repeating the steps discussed above. For example, a medical device is contacted with a composition of the invention three times, allowing the composition to dry on at least one surface of the medical device prior to contacting the medical device with the composition for each subsequent layer. In other words, the medical device can include three coats, or layers, of the composition on at least one surface of the medical device. Further, coatings or layers are also possible.

In another embodiment, a method for coating a medical device with a composition of the invention includes incorporating the composition into the material forming the medical device during formation of the medical device. For example, the composition may be combined with materials forming the medical device, e.g., silicone, polyurethane, polyvinyl chloride, polyethylene, polytetrafluoroethylene, polyethylene terephthalate, and/or polypropylene, and extruded with the material forming the medical device, thereby incorporating the composition into material forming the medical device. In this embodiment, the composition may be incorporated in a septum or adhesive, which is placed at a medical device insertion or implantation site.

Examples of devices that can be coated using the compositions of the invention include tubing and other surface medical devices, such as urinary catheter, mucous extraction catheter, suction catheter, umbilical cannula, contact lenses, intrauterine devices, intravaginal and intraintestinal devices, endotracheal tubes, bronchoscopes, dental prostheses and orthodontic devices, surgical instruments, dental instruments, tubing, dental water lines, dental drain tubes, fabrics, paper, indicator strips (e.g., paper indicator strips or plastic indicator strips), adhesives (e.g., hydrogel adhesives, hot-melt adhesives, or solvent-based adhesives), bandages, tissue dressings or healing devices and occlusive patches, and any other surface devices used in the medical field. Devices may include electrodes, external prostheses, fixation tapes, compression bandages, and monitors of various types. Medical devices also include any device that may be placed at the insertion or implantation site such as the skin near the insertion or implantation site, and which include at least one surface which is susceptible to colonization by biofilm embedded microorganisms. In one specific embodiment, a composition of the invention is integrated into an adhesive, such as tape, thereby providing an adhesive, which may prevent growth or proliferation of biofilm embedded microorganisms on at least one surface of the adhesive. Medical devices for the present invention include surfaces of equipment in operating rooms, emergency rooms, hospital rooms, clinics, and bathrooms.

In another aspect, the invention provides a method for reducing biofilm microorganisms from at least one surface of the medical device. In one specific embodiment, the method of reducing biofilm formation from at least one surface of the medical device includes contacting the medical device with a composition of the invention. "Contacting" includes, but is not limited to, soaking, rinsing, flushing, submerging, and washing. A medical device should be contacted with a composition of the invention for a period of time sufficient to substantially reduce a biofilm from at least one surface of a medical device. In one specific embodiment, a medical device is submerged in a composition for at least 5 minutes. Alternatively, a medical device may be flushed with a composition. In the example of tubing, such as dental drain tubing (dental water line), a composition of the invention may be poured into the dental drain tubing and both ends of the tubing clamped such that the composition is retained within the lumen of the tubing. The tubing is then allowed to remain filled with the composition for a period of time sufficient to substantially reduce or remove all of the microorganisms from at least one surface of the medical device, generally, for at least about 1 minute to about 48 hours. Alternatively, the tubing may be flushed by pouring the composition into the lumen of the tubing for an amount of time sufficient to substantially reduce or remove all biofilm growth.

The concentration of active ingredients in a composition of the invention may vary as desired or necessary to decrease the amount of time the composition is in contact with the medical device.

In embodiments of the invention, a step of forming a composition of the invention may also include one or more of steps of adding an organic solvent, a medical device material penetrating agent, or an alkalinizing agent to the composition in order to enhance reactivity of a surface of a medical device with the composition. In an embodiment of coating medical devices, an organic solvent, medical device material penetrating agent, and/or alkalinizing agent preferably facilitate adhesion of a composition of the invention to at least one surface of a medical device.

In one embodiment, a device is placed in contact with a composition of the invention by dipping the device in the composition for about 30 minutes to about 120 minutes at a temperature from about 35° C. to about 65° C. A device may be placed in contact with a composition of the invention by dipping the device in the composition for about 120 minutes at a temperature of about 45° C. The device is then removed from the composition, and the composition on the surface of the device is allowed to dry. The medical device may be placed in an oven or other heated environment for a period of time sufficient for the composition to dry.

In another embodiment, a method for coating medical devices with a composition of the invention includes forming a coating of an effective concentration to substantially reduce the growth, proliferation, or colonization of biofilm microorganisms on at least one surface of the medical device by dissolving an active ingredient in an organic solvent, combining a medical device material penetrating agent to active ingredients and organic solvent, and combining an alkalinizing agent to improve reactivity of a surface of the medical device. The composition is then heated to a temperature of about 35° C. to about 65° C. to enhance adherence of the composition to at least one surface of the device. A composition coating is applied to at least one surface of the medical device, for example, contacting a coating of a composition of the invention to the at least one surface of a medical device for a sufficient period of time for the composition coating to adhere to at least one surface of the medical device. The medical device is removed from the composition coating and allowed to dry for at least 8 hours, and preferably overnight, at room temperature. The medical device may then be rinsed with a liquid, such as water, and allowed to dry for at least 2 hours, and preferably 8 hours, before being sterilized. To facilitate drying of a composition onto a surface of a medical device, the medical device may be placed into a heated environment such as an oven.

Wound Care Wounds often have multiple barriers to healing. Wound healing and infection is influenced by the relationship between the ability of bacteria to create a stable, prosperous community within a wound environment and the ability of the host to control the bacterial community. Since bacteria are rapidly able to form their own protective microenvironment (biofilm) following their attachment to a surface, the ability of the host to control these organisms is likely to decrease as the biofilm community matures. Within a stable biofilm community, interactions between aerobic and anaerobic bacteria are likely to increase their net pathogenic effect, enhancing their potential to cause infection and delay healing. Biofilms have been linked to chronic wounds: microscopic evaluation of chronic wounds showed well organized biofilm with extracellular polymeric substance adhered around colony bacteria in at least 60% of the chronic wounds (Mertz, Wounds, 15: 1-9, 2003).

In addition to a direct effect on wound healing by the production of destructive enzymes and toxins, mixed communities of microorganisms may also indirectly affect healing by promoting a chronic inflammatory state. Prolonged exposure to bacteria within a chronic wound leads to a prolonged inflammatory response, resulting in the release of free radicals and numerous lytic enzymes that could have a detrimental effect on cellular processes involved in wound healing. Proteinases released from a number of bacteria, particularly P. aeruginosa, are known to affect growth factors and many other tissue proteins that are necessary for the wound healing process (Steed et al., J. Am. Coll. Surg, 183:61-64, 1996; Travis et al., Trends Microbiol. 3:405-407, 1995). The increased production of exudates that often accompanies increased microbial load has been associated with the degradation of growth factors and matrix metalloproteinases (MMPs), which subsequently affect cell proliferation and wound healing (Falanga et al., J Invest Dermatol. 1:125-127, 1994).

A method of the invention includes treating, cleaning, or disinfecting a wound by administering a composition of the invention. A method of the invention also includes treating, cleaning, or disinfecting a wound by contacting the wound with a wound care device of the invention, wherein the wound care device includes a composition of the invention. Such wounds include chronic wounds, acute wounds, surgical wounds, surgical sites, second and third degree burns, stasis ulcers, tropic lesions, decubitus ulcers, severe cuts, and abrasions. Wound care devices include, but are not limited to, dressings and bandages. A composition of the invention can also be formulated as a gel or an ointment.

Caries/Periodontal Diseases

Caries and periodontal diseases are two of the most common chronic infectious diseases affecting humankind and are associated with dental plaque, which is a biofilm on tooth surfaces. Streptococci account for approximately 20% of the salivary bacteria, which include *Streptococcus* spp. such as *Streptococcus mutans, Streptococcus sobrinus, Streptococcus sanguis, Streptococcus gordonii, Streptococcus oralis* and *Streptococcus mitis*. Although four streptococci, *S. mutans, S. sobrinus, S. sanguis* and *S. oralis* are directly involved in the initiation of dental caries, *S. mutans* is considered to be the principal etiological agent of caries (Devulapalle et al., Carbohydr. Res., 339:1029-1034, 2004). Periodontal disease comprises a collection of inflammatory conditions of the periodontium (gingiva, periodontal ligament, cementum, and alveolar bone) due to a chronic bacterial infection, i.e., dental plaque. Over 90% of the population of the United States is affected by periodontal disease (Brown et al., J. Dent. Res. 75:672-683, 1996).

In an embodiment, a composition of the invention can be incorporated into an oral consumable product such as toothpaste, mouth wash, chewing gum, breath mints, dental floss, dentures, mouth guards and similar consumables.

In an embodiment, a method includes treating or preventing caries or periodontal disease in a subject comprising administering a composition of the invention to the subject. In a further embodiment, a method includes treating or preventing caries or periodontal disease in a subject by contacting the biofilm with an oral consumable product comprising a composition of the invention. Periodontal disease includes gingivitis, periodontitis, and acute necrotizing ulcerative gingivitis.

Although the invention has been described with reference to illustrative embodiments, it is to be understood that the invention is not limited to these precise embodiments, and that various changes and modification are to be intended to be encompassed in the appended claims.

EXAMPLES

Example 1

Effect of Protamine Sulfate (PS) and Benzalkonium Chloride (BZK) Alone and in Combination on *Escherichia coli* Growth and Biofilm Formation An overnight broth culture of *E. coli* was grown in TSB and used as inoculum. 96-well microplates containing colony forming antigen medium (for gram-positive species) in the absence and the presence of each compound (PS or BZK) separately and together (PS and BZK) were inoculated and incubated at 26° C. for 24 hours. Growth of planktonic cells based on absorbance at 600 nm using Labsystems Multiskan Ascent microplate reader was determined. Biofilm was measured by discarding the media in the wells, rinsing the well three times with water, and staining the bound cells with crystal violet. The dye was then solubilized with 33% acetic acid, and absorbance at 630 nm was determined using a microtiter plate reader. A composition comprising PS and BZK showed an enhanced inhibitory effect on biofilm formation, as compared to either PS or BZK alone (FIG. 1; Table 1).

TABLE 1

Inhibitory effect of protamine sulfate (PS; 12 µg/ml) and benzalkonium chloride (BZK; 6 µg/ml) alone and in combination on *Escherichia coli* biofilm*

| Pathogen | Biofilm Inhibition by | | Expected Biofilm Inhibition by (Additive) | Unexpected Biofilm Inhibition by (More than additive) |
| --- | --- | --- | --- | --- |
| | PS | BZK | PS + BZK | PS + BZK |
| E. coli | 0.04 | 0.14 | 0.19 | 0.32 |

*As determined by the reduction in biofilm formation in terms of Optical Density (OD) at 630 nm.

Example 2

Figure 2:
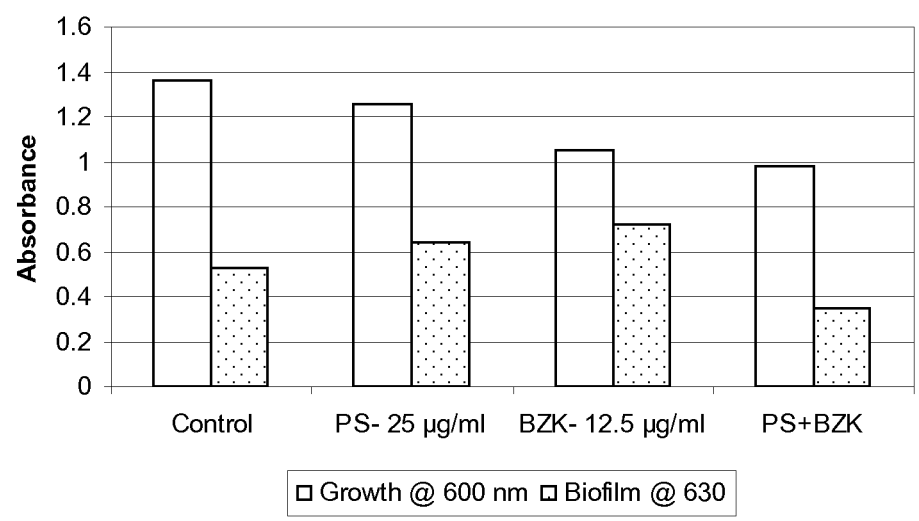
FIG. 2 is a bar graph illustrating the effect of control (solution without an active ingredient), 25 µg/ml of protamine sulfate (PS), 12.5 µg/ml of benzalkonium chloride (BZK) and a combination of 25 µg/ml protamine sulfate and 12.5 µg/ml benzalkonium chloride (PS+BZK) on growth and biofilm formation of Pseudomonas aeruginosa.

Effect of Protamine Sulfate (PS) and Benzalkonium Chloride (BZK) Alone and in Combination on *Pseudomonas aeruginosa* Growth and Biofilm Formation An overnight broth culture of *P. aeruginosa* was grown in TSB and used as inoculum. 96-well microplates containing colony forming antigen medium (for gram-positive species) in the absence and the presence of each compound (PS or BZK) separately and together (PS and BZK) were inoculated and incubated at 26° for 24 hours. Growth of planktonic cells based on absorbance at 600 nm using Labsystems Multiskan Ascent microplate reader was determined. Biofilm was measured by discarding the media in the wells, rinsing the well three times with water, and staining the bound cells with crystal violet. The dye was then solubilized with 33% acetic acid, and absorbance at 630 nm was determined using a microtiter plate reader. A composition comprising PS and BZK showed an enhanced inhibitory effect on biofilm formation, as compared to either PS or BZK alone (FIG. 2; Table 2).

TABLE 2

Inhibitory effect of protamine sulfate (PS; 25 μg/ml) and benzalkonium chloride (BZK; 12.5 μg/ml) alone and in combination on *Pseudomonas aeruginosa* biofilm*

| Pathogen | Biofilm Inhibition by | | Expected Biofilm Inhibition by (Additive) | Unexpected Biofilm Inhibition by (More than additive) |
|---|---|---|---|---|
| | PS | BZK | PS + BZK | PS + BZK |
| P. aeruginosa | 0.00 | 0.00 | 0.00 | 0.18 |

*As determined by the reduction in biofilm formation in terms of Optical Density (OD) at 630 nm.

Example 3

Figure 3:
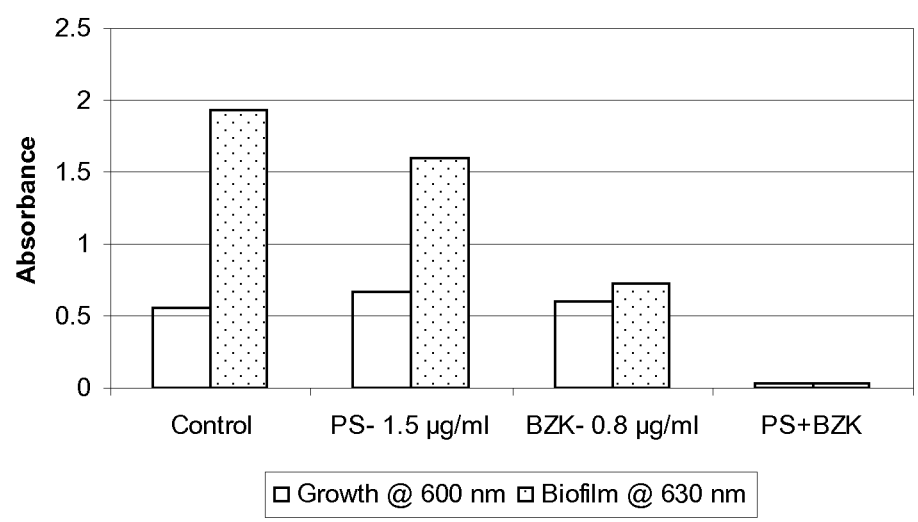
FIG. 3 is a bar graph illustrating the effect of control (solution without an active ingredient), 1.5 µg/ml of protamine sulfate (PS), 0.8 µg/ml of benzalkonium chloride (BZK) and a combination of 1.5 µg/ml protamine sulfate and 0.8 µg/ml benzalkonium chloride (PS+BZK) on growth and biofilm formation of Staphylococcus epidermidis.

Effect of Protamine Sulfate (PS) and Benzalkonium Chloride (BZK) Alone and in Combination on *Staphylococcus epidermidis* Growth and Biofilm Formation An overnight broth culture of S. epidermidis was grown in TSB, and used as inoculum. 96-well microplates containing TSB (for gram-positive species) in the absence and the presence of each compound (PS or BZK) separately and together (PS and BZK) were inoculated and incubated at 37° C. for 24 hours. Growth of planktonic cells based on absorbance at 600 nm using Labsystems Multiskan Ascent microplate reader was determined. Biofilm was measured by discarding the media in the wells, rinsing the well three times with water, and staining the bound cells with crystal violet. The dye was then solubilized with 33% acetic acid, and absorbance at 630 nm was determined using a microtiter plate reader. A composition comprising PS and BZK showed an enhanced inhibitory effect on biofilm formation, as compared to either PS or BZK alone (FIG. 3; Table 3).

TABLE 3

Inhibitory effect of protamine sulfate (PS; 1.5 μg/ml) and benzalkonium chloride (BZK; 0.8 μg/ml) alone and in combination on *Staphylococcus epidermidis* biofilm*

| Pathogen | Biofilm Inhibition by | | Expected Biofilm Inhibition by (Additive) | Unexpected Biofilm Inhibition by (More than additive) |
|---|---|---|---|---|
| | PS | BZK | PS + BZK | PS + BZK |
| S. epidermidis | 0.34 | 1.21 | 1.54 | 1.90 |

*As determined by the reduction in biofilm formation in terms of Optical Density (OD) at 630 nm.

Example 4

Figure 4:
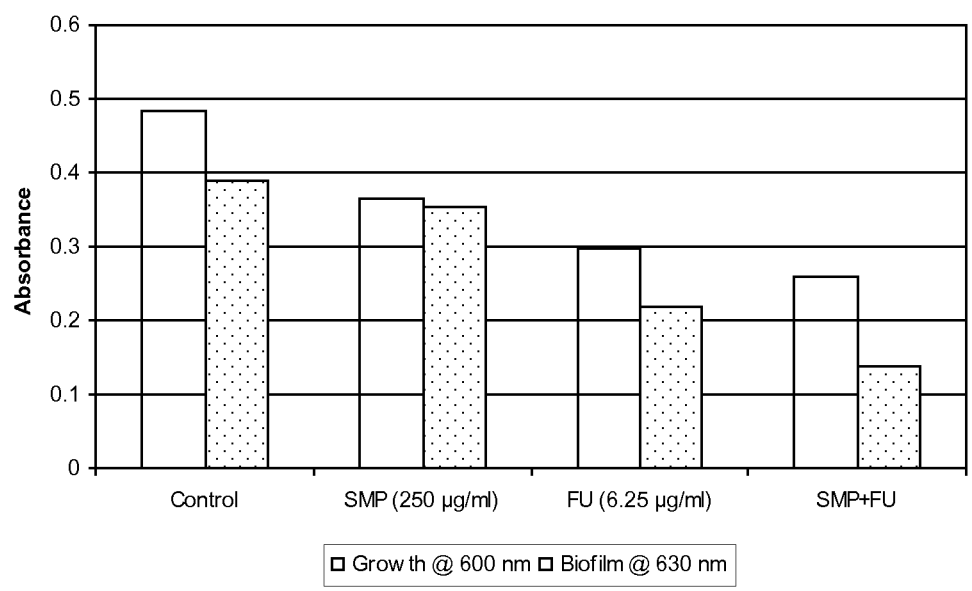
FIG. 4 is a bar graph illustrating the effect of control (solution without an active ingredient), 250 µg/ml of sodium metaperiodate (SMP), 6.25 µg/ml of 5-fluorouracil (FU) and a combination of 250 µg/ml sodium metaperiodate and 6.25 µg/ml 5-fluorouracil (SMP+FU) on growth and biofilm formation of Escherichia coli.

Effect of Sodium Metaperiodate (SMP) and 5-Fluorouracil (FU) Alone and in Combination on *Escherichia coli* Growth and Biofilm Formation An overnight broth culture of E. coli was grown in TSB and used as inoculum. 96-well microtiter plate containing TSB in the absence and presence of each compound separately (SMP or FU) and together (SMP+FU) were inoculated. The biofilm was grown by incubating at 37° C. for 24 hours. Growth of planktonic cells based on absorbance at 600 nm using Labsystems Multiskan Ascent microplate reader was determined. Biofilm was measured by discarding the media in the wells, rinsing the well three times with water, and staining the bound cells with crystal violet. The dye was then solubilized with 33% acetic acid, and absorbance at 630 nm was determined using a microtiter plate reader. A composition comprising SMP and FU showed an enhanced inhibitory effect on E. coli biofilm formation, as compared to either SMP or FU alone (FIG. 4; Table 4).

TABLE 4

Inhibitory effect of sodium metaperiodate (SMP; 250 μg/ml) and 5-fluorouracil (FU; 6.25 μg/ml) alone and in combination on *Escherichia coli* biofilm*

| Pathogen | Biofilm Inhibition by | | Expected Biofilm Inhibition by (Additive) | Unexpected Biofilm Inhibition by (More than additive) |
|---|---|---|---|---|
| | SMP | FU | SMP + FU | SMP + FU |
| E. coli | 0.3 | 0.17 | 0.21 | 0.25 |

*As determined by the reduction in biofilm formation in terms of Optical Density (OD) at 630 nm Example 5

Figure 5:
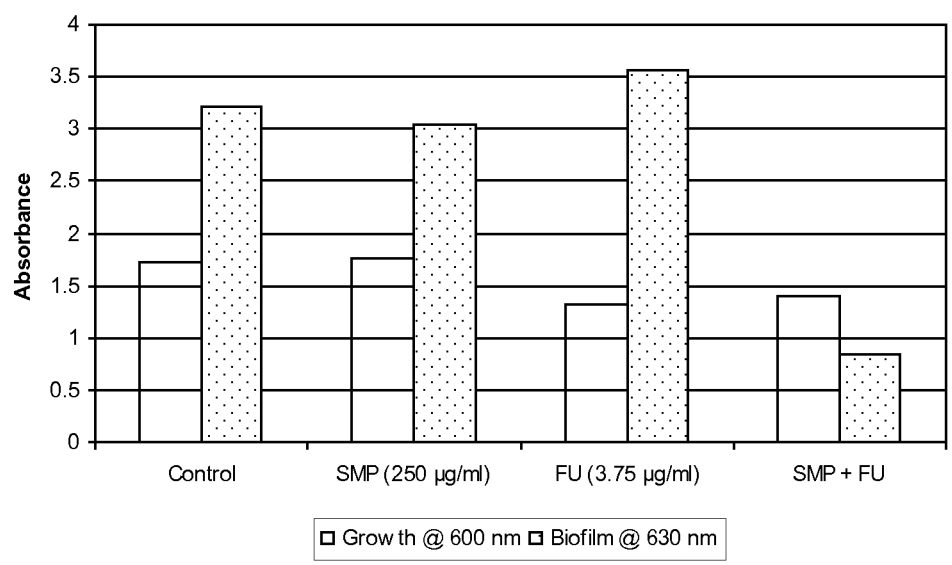
FIG. 5 is a bar graph illustrating the effect of control (solution without an active ingredient), 250 µg/ml of sodium metaperiodate (SMP), 3.75 µg/ml of 5-fluorouracil (FU) and a combination of 250 µg/ml sodium metaperiodate and 3.75 µg/ml 5-fluorouracil (SMP+FU) on growth and biofilm formation of Pseudomonas aeruginosa.

Effect of Sodium Metaperiodate (SMP) and 5-Fluorouracil (FU) Alone and in Combination on *Pseudomonas aeruginosa* Growth and Biofilm Formation An overnight broth culture of P. aeruginosa was grown in TSB and used as inoculum. 96-well microtiter plate containing TSB in the absence and presence of each compound separately (SMP or FU) and together (SMP+FU) were inoculated. The biofilm was grown by incubating at 37° C. for 24 hours. Growth of planktonic cells based on absorbance at 600 nm using Labsystems Multiskan Ascent microplate reader was determined. Biofilm was measured by discarding the media in the wells, rinsing the well three times with water, and staining the bound cells with crystal violet. The dye was then solubilized with 33% acetic acid, and absorbance at 630 nm was determined using a microtiter plate reader. A composition comprising SMP and FU showed an enhanced inhibitory effect on P. aeruginosa biofilm formation, as compared to either SMP or FU alone (FIG. 5; Table 5).

TABLE 5

Inhibitory effect of sodium metaperiodate (SMP; 250 µg/ml) and
5-fluorouracil (FU; 3.75 µg/ml) alone and in combination on
*Pseudomonas aeruginosa* biofilm*

| Pathogen | Biofilm Inhibition by | | Expected Biofilm Inhibition by (Additive) | Unexpected Biofilm Inhibition by (More than additive) |
|---|---|---|---|---|
| | SMP | FU | SMP + FU | SMP + FU |
| P. aeruginosa | 0.16 | 0.00 | 0.16 | 2.37 |

*As determined by the reduction in biofilm formation in terms of Optical Density (OD) at 630 nm.

Example 6

Figure 6:
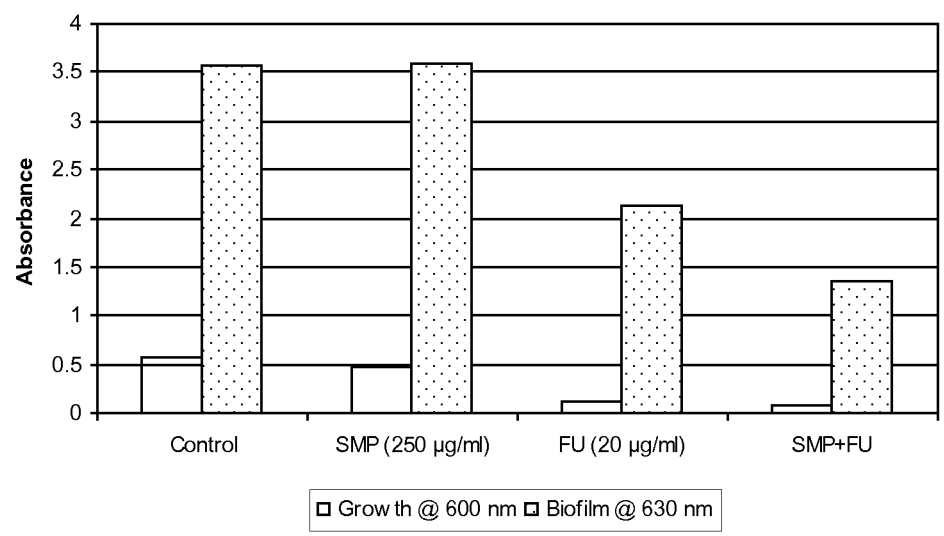
FIG. 6 is a bar graph illustrating the effect of control (solution without an active ingredient), 250 µg/ml of sodium metaperiodate (SMP), 20 µg/ml of 5-fluorouracil (FU) and a combination of 250 µg/ml sodium metaperiodate and 20 µg/ml 5-fluorouracil (SMP+FU) on growth and biofilm formation of Staphylococcus epidermidis.

Effect of Sodium Metaperiodate (SMP) and 5-Fluorouracil (FU) Alone and in Combination on *Staphylococcus epidermidis* Growth and Biofilm Formation An overnight broth culture of *S. epidermidis* was grown in TSB and used as inoculum. 96-well microtiter plate containing TSB in the absence and presence of each compound separately (SMP or FU) and together (SMP+FU) were inoculated. The biofilm was grown by incubating at 37° C. for 24 hours. Growth of planktonic cells based on absorbance at 600 nm using Labsystems Multiskan Ascent microplate reader was determined. Biofilm was measured by discarding the media in the wells, rinsing the well three times with water, and staining the bound cells with crystal violet. The dye was then solubilized with 33% acetic acid, and absorbance at 630 nm was determined using a microtiter plate reader. A composition comprising SMP and FU showed an enhanced inhibitory effect on *S. epidermidis* biofilm formation, as compared to either SMP or FU alone (FIG. 6; Table 6).

TABLE 6

Inhibitory effect of sodium metaperiodate (SMP; 250 µg/ml) and
5-fluorouracil (FU; 20 µg/ml) alone and in combination on
*Staphylococcus epidermidis* biofilm*

| Pathogen | Biofilm Inhibition by | | Expected Biofilm Inhibition by (Additive) | Unexpected Biofilm Inhibition by (More than additive) |
|---|---|---|---|---|
| | SMP | FU | SMP + FU | SMP + FU |
| S. epidermidis | 0.00 | 1.43 | 1.43 | 2.22 |

* As determined by the reduction in biofilm formation in terms of Optical Density (OD) at 630 nm.

Example 7

Figure 7:
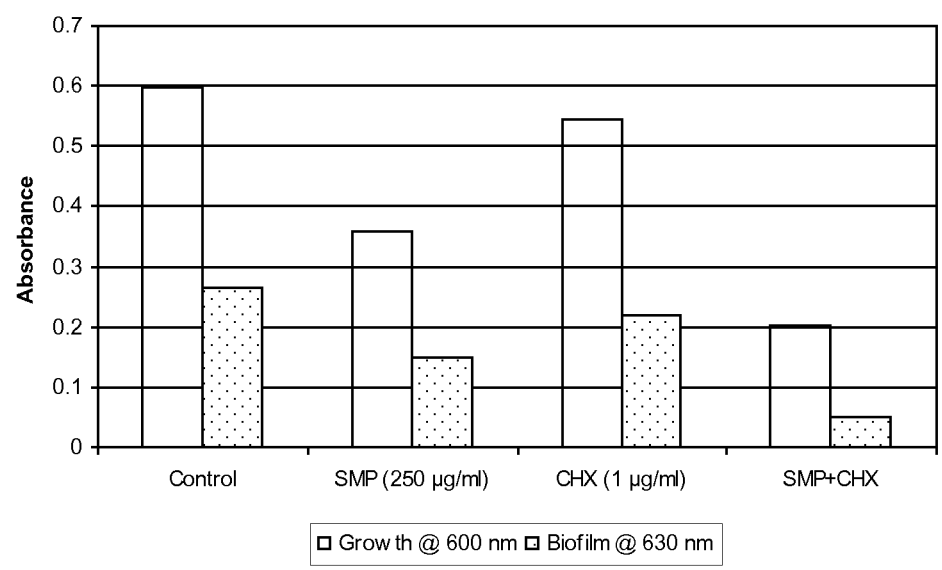
FIG. 7 is a bar graph illustrating the effect of control (solution without an active ingredient), 250 µg/ml of sodium metaperiodate (SMP), 1 µg/ml of chlorhexidine (CHX) and a combination of 250 µg/ml sodium metaperiodate and 1 µg/ml chlorhexidine (SMP+CHX) on growth and biofilm formation of Escherichia coli.

Effect of Sodium Metaperiodate (SMP) and Chlorhexidine (CHX) Alone and in Combination on *Escherichia coli* Growth and Biofilm Formation An overnight broth culture of *E. coli* was grown in TSB and used as inoculum. 96-well microtiter plate containing TSB in the absence and presence of each compound separately (SMP or CHX) and together (SMP+CHX) were inoculated. The biofilm was grown by incubating at 37° C. for 24 hours. Growth of planktonic cells based on absorbance at 600 nm using Labsystems Multiskan Ascent microplate reader was determined. Biofilm was measured by discarding the media in the wells, rinsing the well three times with water, and staining the bound cells with crystal violet. The dye was then solubilized with 33% acetic acid, and absorbance at 630 nm was determined using a microtiter plate reader. A composition comprising SMP and CHX showed an enhanced inhibitory effect on *E. coli* biofilm formation, as compared to either SMP or CHX alone (FIG. 7; Table 7).

TABLE 7

Inhibitory effect of sodium metaperiodate (SMP; 250 µg/ml) and
chlorhexidine (CHX; 1 µg/ml) alone and in combination on
*Escherichia coli* biofilm*

| Pathogen | Biofilm Inhibition by | | Expected Biofilm Inhibition by (Additive) | Unexpected Biofilm Inhibition by (More than additive) |
|---|---|---|---|---|
| | SMP | CHX | SMP + CHX | SMP + CHX |
| E. coli | 0.12 | 0.04 | 0.16 | 0.22 |

*As determined by the reduction in biofilm formation in terms of Optical Density (OD) at 630 nm.

Example 8

Figure 8:
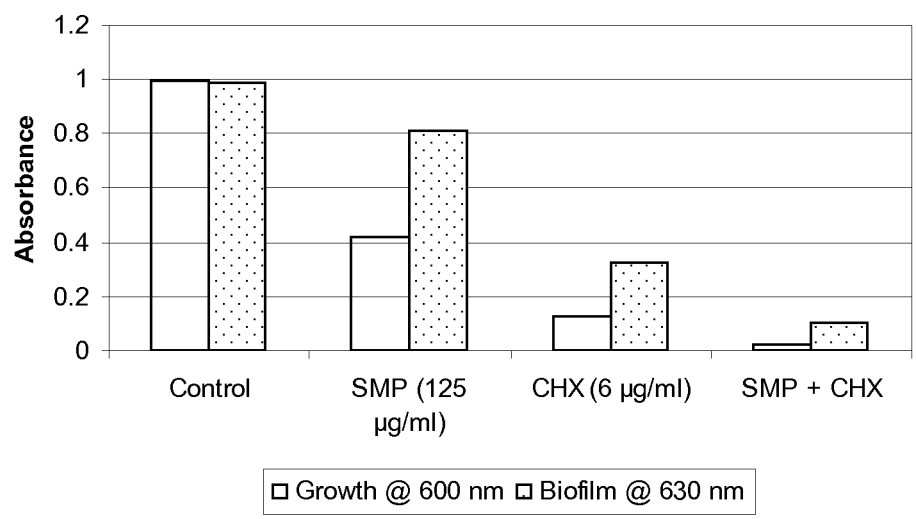
FIG. 8 is a bar graph illustrating the effect of control (solution without an active ingredient), 125 µg/ml of sodium metaperiodate (SMP), 6 µg/ml of chlorhexidine (CHX) and a combination of 125 µg/ml sodium metaperiodate and 6 µg/ml chlorhexidine (SMP+CHX) on growth and biofilm formation of Pseudomonas aeruginosa.

Effect of Sodium Metaperiodate (SMP) and Chlorhexidine (CHX) Alone and in Combination on *Pseudomonas aeruginosa* Growth and Biofilm Formation An overnight broth culture of bacteria and yeast were grown in TSB and used as inoculum. 96-well microplates containing TSB (for gram-positive species and yeast) and colony forming unit antigen medium (for gram-negative bacteria) in the absence and the presence of each compound separately (SMP or CHX) and together (SMP+CHX) were inoculated. The biofilm was grown by incubating at 37° C. (for gram-positive bacteria and yeast) and 26° C. (for gram-negative bacteria) for 24 hours. Growth of planktonic cells based on absorbance at 600 nm using Labsystems Multiskan Ascent microplate reader was determined. Biofilm was measured by discarding the media in the wells, rinsing the well three times with water, and staining the bound cells with crystal violet. The dye was then solubilized with 33% acetic acid, and absorbance at 630 nm was determined using a microtiter plate reader. A composition comprising SMP and CHX showed an enhanced inhibitory effect on *P. aeruginosa* biofilm formation, as compared to either SMP or CHX alone (FIG. 8; Table 8).

TABLE 8

Inhibitory effect of sodium metaperiodate (SMP; 125 µg/ml) and
chlorhexidine (CHX; 6 µg/ml) alone and in combination on
*Pseudomonas aeruginosa* biofilm*

| Pathogen | Biofilm Inhibition by | | Expected Biofilm Inhibition by (Additive) | Unexpected Biofilm Inhibition by (More than additive) |
|---|---|---|---|---|
| | SMP | CHX | SMP + CHX | SMP + CHX |
| P. aeruginosa | 0.17 | 0.66 | 0.83 | 0.88 |

*As determined by the reduction in biofilm formation in terms of Optical Density (OD) at 630 nm

Example 9

Figure 9:
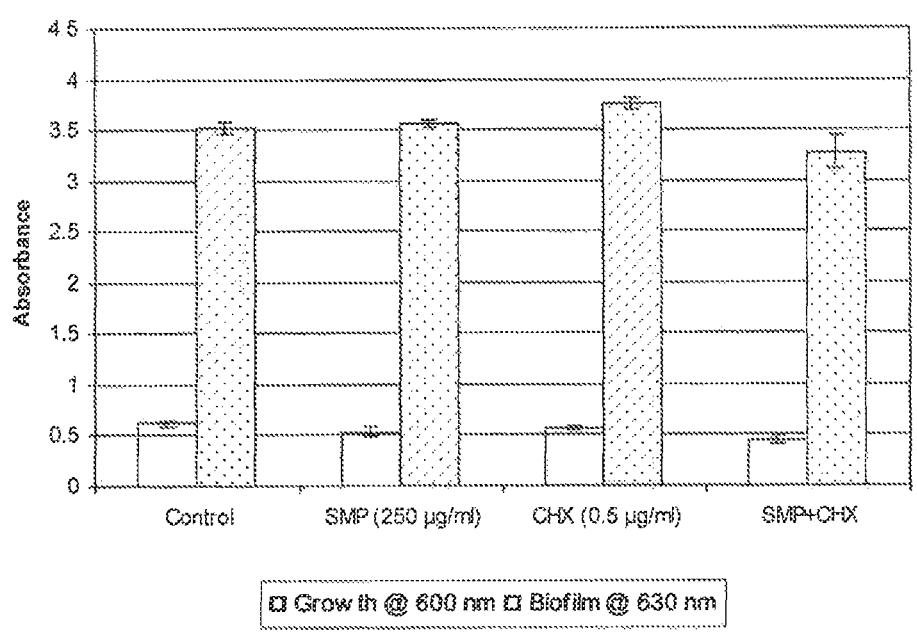
FIG. 9 is a bar graph illustrating the effect of control (solution without an active ingredient), 250 µg/ml of sodium metaperiodate (SMP), 0.5 µg/ml of chlorhexidine (CHX) and a combination of 250 µg/ml sodium metaperiodate and 0.5 µg/ml chlorhexidine (SMP+CHX) on growth and biofilm formation of Staphylococcus epidermidis.

Effect of Sodium Metaperiodate (SMP) and Chlorhexidine (CHX) Alone and in Combination on *Staphylococcus epidermidis* Growth and Biofilm Formation An overnight broth culture of *S. epidermidis* was grown in TSB and used as inoculum. 96-well microtiter plate containing TSB in the absence and presence of each compound separately (SMP or CHX) and together (SMP+CHX) were inoculated. The biofilm was grown by incubating at 37° C. for 24 hours. Growth of planktonic cells based on absorbance at 600 nm using Labsystems Multiskan Ascent microplate reader was determined. Biofilm was measured by discarding the media in the wells, rinsing the well three times with water, and staining the bound cells with crystal violet. The dye was then solubilized with 33% acetic acid, and absorbance at 630 nm was determined using a microtiter plate reader. A composition comprising SMP and CHX showed an enhanced inhibitory effect on *S. epidermidis* biofilm formation, as compared to either SMP or CHX alone (FIG. 9; Table 9).

TABLE 9

Inhibitory effect of sodium metaperiodate (SMP; 250 μg/ml) and chlorhexidine (CHX; 0.5 μg/ml) alone and in combination on *Staphylococcus epidermidis* biofilm*

| Pathogen | Biofilm Inhibition by | | Expected Biofilm Inhibition by (Additive) | Unexpected Biofilm Inhibition by (More than additive) |
| --- | --- | --- | --- | --- |
| | SMP | CHX | SMP + CHX | SMP + CHX |
| *S. epidermidis* | 0.00 | 0.00 | 0.00 | 0.24 |

*As determined by the reduction in biofilm formation in terms of Optical Density (OD) at 630 nm

Example 10

Antimicrobial Activity of Protamine Sulfate (PS) and Silver Nanoparticles (SNP) Alone and in Combination Against Medical Device-Associated Pathogens Bacterial strains were grown overnight at 37° C. with 100 rpm shaking in Tryptic Soy Broth (TSB) and diluted to approximately $10^5$ CFU/ml. Assays were conducted by methods of minimum inhibitory concentration (MIC) in 96-well microtiter plates as described previously (Amsterdam, D. 1996, In: V. Loman, Ed., "Antibiotics in laboratory medicine", p. 52-111, Williams and Wilkins, Baltimore, M.D.). Antimicrobials PS and SNP both alone and together were serially diluted in TSB (100 μl), and 100 μl of bacterial suspension was added to each well. Plates were incubated at 37° C. for 24 hours and read at 600 nm using a microtiter plate reader (Multiskan Ascent, Labsystems, Helsinki, Finland). A compositions comprising PS and SNP showed an enhanced inhibitory effect on bacterial growth as compared to either PS or SNP above, as shown in Table 10.

TABLE 10

Minimal inhibitory concentrations (MICs) of protamine sulfate (PS), silver nanoparticles (SNP) alone and in combination against medical device associated pathogens

| | MIC (μg/ml) | | |
| --- | --- | --- | --- |
| Pathogen | PS | SNP | PS + SNP |
| *S. aureus* | >200 | >1000 | 100 + 500 |
| *Escherichia coli* | >200 | >1000 | 200 + 1000 |

Example 11

Broad-Spectrum Antimicrobial Activity of Sodium Metaperiodate (SMP) and Chlorhexidine (CHX) Disinfectant Formulation A disinfectant was formulated containing 0.15% chlorhexidine (CHX) and 0.025% sodium metaperiodate (SMP). The antimicrobial activity was tested against Gram positive and Gram negative bacteria using the AOAC "use dilution" method. Stainless steel penicylinders were soaked for 15 minutes in a broth culture of the test organism to form a bacterial film. The carriers with bacterial film were then removed and dried for approximately 30 minutes at 37° C. This now represents a nonporous, hard, inanimate surface contaminated with a dried film of bacteria. The contaminated carriers were exposed to 10 ml of the disinfectant for 10 minutes at 20° C. After treatment; the carriers were removed from the disinfectant and placed in 10 ml subculture broth media containing appropriate neutralizers. The subculture tubes were incubated 48 hours at 37° C. The tubes were examined for growth as determined by the turbidity of the media. The disinfectant formulation was effective against all the pathogens tested.

TABLE 11

Broad-Spectrum Antimicrobial Activity of SMP-CHX Disinfectant Formulation on Gram Positive and Gram Negative Bacteria

| | Number of Carriers | |
| --- | --- | --- |
| Test Organism | Exposed | Showing Growth |
| *Staphylococcus aureus* (ATCC 6538) | 180 | 0 |
| *Pseudomonas aeruginosa* (ATCC 15442) | 180 | 0 |
| *Salmonella choleraesuis* (ATCC 10708) | 180 | 0 |
| *Escherichia coli* O157:H7 | 20 | 0 |
| *E. coli* (ATCC 25404) | 20 | 0 |
| *Acinetobacter baumannii* | 20 | 0 |
| Methicillin-resistant *S. aureus* (MRSA) | 20 | 0 |
| Vancomycin-resistant *Enterococci* (VRE) | 20 | 0 |
| *Listeria monocytogenes* | 20 | 0 |
| *Klebsiella pneumoniae* | 20 | 0 |
| *Campylobacter jejuni* (ATCC 33560) | 20 | 0 |

We claim:

1. A composition for removing or reducing a microbial biofilm formed by *S. epidermidis*, the composition comprising:
   (a) a metaperiodate or a metaperiodate salt in a concentration of about 250 μg/ml and
   (b) chlorhexidine or a chlorohexidine salt in a concentration of about 0.5 μg/ml.

2. The composition of claim 1, wherein the metaperiodate is preferably selected from sodium metaperiodate or potassium metaperiodate.

3. The composition according to claim 1, wherein said composition is incorporated in a product selected from the group consisting of a toothbrush; dental floss; a denture, a mouth guard; a dairy line; a dairy line filter; a water line; a line used in food and beverage manufacturing; a general household disinfectant; a laundry detergent; cleaning supplies; equipment involved in the leeching process or mining; wound care; a vacuum system; an HVAC system; a vacuum cleaner bag; paint covering; a wall covering; a window frame; a door; a door frame; a cooling tower; a humidifier; a vacuum cleaning a filter; a toy; a cosmetic container; a plastic bottle; a water jug; a tap and water spout; a washing machine; a dishwasher; an animal water dish; a bathroom tile; a bathroom fixture; a sink; a shower; a shower heat; a toilet; a toilet lid; a toilet seat; a sealant; grout; a towel; a home and kitchen container; a dish; a cup; an utensil; a bowl; a food storage container; a beverage storage container; a cutting board; a dish drying tray; a garbage bag; a bathtub; a whirlpool; an aerated bathtub; a sink; a shower; a fish pond; a swimming pool; a swimming pool liner; a swimming pool skimmer; a pond liner; a bird bath; a garden hose; a water sprinkling line; a planter; and a hot tub.

4. The composition according to claim 1, further comprising an additive selected from the group consisting of water, ethanol, bleach constituent or an oxidizing constituents, a binding or bonding or coupling agent, a wetting agent, an odor absorbing agent, a levelling agent, an adherent, a thickener, an antistatic agent, an optical brightening compound, an opacifier, a nucleating agent, an antioxidant, a UV stabilizer, a filler, a permanent press finish, a softener, a lubricant, a curing accelerator, an adhesive, a bis-phenol, a biguanide, a silver compound, a 5-fluorouracil, a bisphosphonate, a gallium compound, a bismuthiol, a chelating agent, a cationic polypeptide, a quaternary ammonium compound, a maleimide, an antibiotic, a pH adjuster, a buffer solution, phosphate buffered saline, saline, polyvinyl chloride, polyethylene, polyurethane, polypropylene, silicone, a polycarboxylic acid, a polycarboxylic acid anhydride, a polyamine, a polyamine ions, a polyammonium ion, and polysulfonates, collodion, nylon, rubber, plastic, a polyester, polyethylene tetraphthalate, polytetrafluoroethylene, latex and derivatives thereof, an elastomer, polyethylene tetraphthalate sealed with gelatin, collagen or albumin, a cyanoacrylate, a methacrylate, a paper with porous barrier films, an adhesive, a linear copolymers, a cross-linked copolymer, a graft polymer, a block polymer, or a combination thereof.

5. The composition according to claim 4, wherein said silicone is silicone elastomers, silicone adhesives or a combination thereof.

6. The composition according to claim 4, wherein said polycarboxylic acid is selected from a group consisting of polyacrylic acid, polymethacrylic acid, polymaleic acid, poly-(maleic acid monoester), polyaspartic acid, polyglutamic acid, aginic acid, pectimic acid, or a combination thereof.

7. The composition according to claim 4, wherein said polycarboxylic acid anhydride is selected from a group consisting of polymaleic anhydride, polymethacrylic anhydride, polyacrylic acid anhydride, or a combination thereof.

8. The composition according to claim 4, wherein said polyamine ions is selected from a group consisting of polyethylene imine, polyvinylamine, polylysine, poly-(dialkylamineoethyl methacrylate), poly-(dialkylaminomethyl styrene), poly-(vinylpyridine), or a combination thereof.

9. The composition according to claim 4, wherein said polyammonium ion is selected from a group consisting of poly-(2-methacryloxyethyl trialkyl ammonium ion), poly-(vinylbenzyl trialkyl ammonium ions), poly-(N.N.-alkylypyridinium ion), poly-(dialkyloctamethylene ammonium ion), or a combination thereof.

10. The composition according to claim 4, wherein said polysulfonates is poly-(vinyl sulfonate), poly-(styrene sulfonate), or a combination thereof.

11. The composition according to claim 4, wherein said adhesive is selected from a group consisting of hot melt adhesives, solvent based adhesives, adhesive hydrogels, fabrics, crosslinked hydrogels, non-crosslinked hydrogels, or a combination thereof.

* * * * *